United States Patent
Carroll et al.

(10) Patent No.: US 8,024,202 B2
(45) Date of Patent: Sep. 20, 2011

(54) ERGONOMICS-BASED HEALTH FACILITATOR FOR COMPUTER USERS

(75) Inventors: Randolph W. Carroll, Raleigh, NC (US); Ciaran A. Dellafera, Cambridge, MA (US); Pamela K. Isom, Highlands Ranch, CO (US)

(73) Assignee: International Business Machines Corporation, Armonk, NY (US)

( * ) Notice: Subject to any disclaimer, the term of this patent is extended or adjusted under 35 U.S.C. 154(b) by 334 days.

(21) Appl. No.: 12/249,407

(22) Filed: Oct. 10, 2008

(65) Prior Publication Data

US 2010/0094645 A1   Apr. 15, 2010

(51) Int. Cl.
  *G06Q 10/00* (2006.01)
  *G06Q 50/00* (2006.01)
(52) U.S. Cl. ................... 705/3; 705/2; 702/150
(58) Field of Classification Search .......... 705/2–3, 705/7; 702/150
  See application file for complete search history.

(56) References Cited

U.S. PATENT DOCUMENTS

| | | | |
|---|---|---|---|
| 5,570,301 A | 10/1996 | Barrus | |
| 6,682,351 B1 | 1/2004 | Abraham-Fuchs et al. | |
| 7,258,653 B2 | 8/2007 | Brandon et al. | |
| 7,315,249 B2 | 1/2008 | Littell | |
| 2001/0031451 A1* | 10/2001 | Sander et al. | 434/236 |
| 2002/0118163 A1 | 8/2002 | Rozas | |
| 2004/0077975 A1 | 4/2004 | Zimmerman | |
| 2007/0083384 A1 | 4/2007 | Geslak et al. | |
| 2007/0149360 A1 | 6/2007 | Narayanaswami | |
| 2007/0179648 A1* | 8/2007 | Taylor et al. | 700/90 |
| 2008/0136650 A1 | 6/2008 | Littell | |
| 2009/0030767 A1* | 1/2009 | Morris et al. | 705/9 |

* cited by examiner

*Primary Examiner* — Luke Gilligan
(74) *Attorney, Agent, or Firm* — John R. Pivnichny; Law Office of Jim Boice

(57) ABSTRACT

A method, system and computer program product for facilitating ergonomics-based health in a user of a computer workstation is presented. The method includes the steps of detecting an ergonomics problem for a user of a computer workstation, wherein the ergonomics problem is directly related to a current real-time body position of the user, and wherein the ergonomics problem would likely cause an injury to the user if left uncorrected. A user health protection algorithm is then executed to generate an ergonomic recommendation. The user health protection algorithm utilizes user work parameters as inputs. The ergonomic recommendation, which will correct the ergonomics problem, is then presented to the user.

20 Claims, 7 Drawing Sheets

ERGONOMICS-BASED HEALTH FACILITATOR FOR COMPUTER USERS

BACKGROUND OF THE INVENTION

1. Technical Field

The present disclosure relates to the field of computers, and specifically to computer workstations. Still more particularly, the present disclosure relates to assisting computer users in managing ergonomic issues related to computer workstations.

2. Description of the Related Art

Ergonomics is the field of industrial engineering that deals with how humans interact with equipment and the ambient environment while performing certain tasks. Failure to incorporate proper ergonomics practices, such as improper equipment design, poor tasks design, and/or lack of environmental controls can cause a wide range of injuries to a person. These injuries include minor and transient injuries, such as mild headaches and muscle pain, to more serious injuries, such as carpal tunnel syndrome. Such injuries are particularly common when a user is working at a computer workstation.

Even at a computer workstation that has been optimally designed with careful consideration to ergonomic factors, a user may still misuse the workstation through improper posture, positioning of wireless input devices, poor work practices, etc. That is, even if a user has been trained in proper ergonomic behavioral practices, failing to consistently practice such behavior may expose the user to injury.

SUMMARY OF THE INVENTION

A method, system and computer program product for facilitating ergonomics-based health in a user of a computer workstation is presented. The method includes the steps of detecting an ergonomics problem for a user of a computer workstation, wherein the ergonomics problem is directly related to a current real-time body position of the user, and wherein the ergonomics problem would likely cause an injury to the user if left uncorrected. A user health protection algorithm is then executed to generate an ergonomic recommendation. The user health protection algorithm utilizes user work parameters as inputs. The ergonomic recommendation, which will correct the ergonomics problem, is then presented to the user.

The above, as well as additional purposes, features, and advantages of the present invention will become apparent in the following detailed written description.

BRIEF DESCRIPTION OF THE DRAWINGS

The novel features believed characteristic of the invention are set forth in the appended claims. The invention itself, however, as well as a preferred mode of use, further purposes and advantages thereof, will best be understood by reference to the following detailed description of an illustrative embodiment when read in conjunction with the accompanying drawings, where:

DETAILED DESCRIPTION OF THE PREFERRED EMBODIMENT

Figure 1:
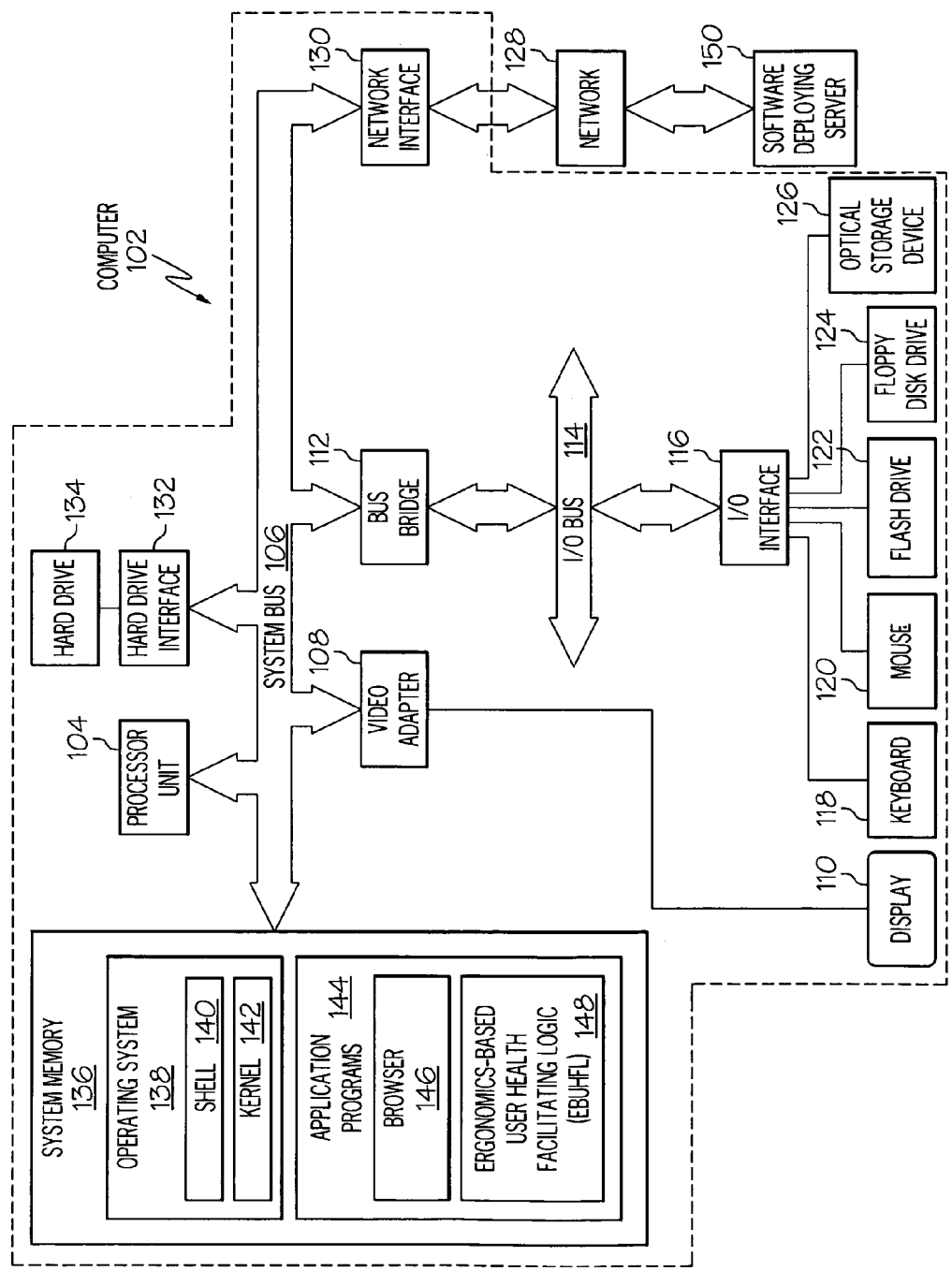
FIG. 1 depicts an exemplary computer which may be utilized by the present invention.

With reference now to the figures, and in particular to FIG. 1, there is depicted a block diagram of an exemplary computer 102, which the present invention may utilize. Note that some or all of the exemplary architecture shown for computer 102 may be utilized by software deploying server 150.

Computer 102 includes a processor unit 104, which may utilize one or more processors each having one or more processor cores, that is coupled to a system bus 106. A video adapter 108, which drives/supports a display 110, is also coupled to system bus 106. System bus 106 is coupled via a bus bridge 112 to an Input/Output (I/O) bus 114. An I/O interface 116 is coupled to I/O bus 114. I/O interface 116 affords communication with various I/O devices, including a keyboard 118, a mouse 120, a Flash Drive 122, a printer 124, and an optical storage device 126 (e.g., a CD-ROM drive). The format of the ports connected to I/O interface 116 may be any known to those skilled in the art of computer architecture, including but not limited to Universal Serial Bus (USB) ports.

Computer 102 is able to communicate with a software deploying server 150 via network 128 using a network interface 130, which is coupled to system bus 106. Network 128 may be an external network such as the Internet, or an internal network such as an Ethernet or a Virtual Private Network (VPN).

A hard drive interface 132 is also coupled to system bus 106. Hard drive interface 132 interfaces with a hard drive 134. In a preferred embodiment, hard drive 134 populates a system memory 136, which is also coupled to system bus 106. System memory is defined as a lowest level of volatile memory in computer 102. This volatile memory includes additional higher levels of volatile memory (not shown), including, but not limited to, cache memory, registers and buffers. Data that populates system memory 136 includes computer 102's operating system (OS) 138 and application programs 144.

OS 138 includes a shell 140, for providing transparent user access to resources such as application programs 144. Generally, shell 140 is a program that provides an interpreter and an interface between the user and the operating system. More specifically, shell 140 executes commands that are entered into a command line user interface or from a file. Thus, shell 140, also called a command processor, is generally the highest level of the operating system software hierarchy and serves as a command interpreter. The shell provides a system prompt, interprets commands entered by keyboard, mouse, or other user input media, and sends the interpreted command(s) to the appropriate lower levels of the operating system (e.g., a kernel 142) for processing. Note that while shell 140 is a text-based, line-oriented user interface, the present invention will equally well support other user interface modes, such as graphical, voice, gestural, etc.

As depicted, OS 138 also includes kernel 142, which includes lower levels of functionality for OS 138, including providing essential services required by other parts of OS 138 and application programs 144, including memory management, process and task management, disk management, and mouse and keyboard management.

Application programs 144 include a renderer, shown in exemplary manner as a browser 146. Browser 146 includes program modules and instructions enabling a World Wide Web (WWW) client (i.e., computer 102) to send and receive network messages to the Internet using HyperText Transfer Protocol (HTTP) messaging, thus enabling communication with software deploying server 150 and other described computer systems.

Application programs 144 in computer 102's system memory (as well as software deploying server 150's system memory) also include an Ergonomics-Based User Health Facilitating Logic (EBUHFL) 148. EBUHFL 148 includes code for implementing the processes described below, and particularly as described in FIGS. 2-7. In one embodiment, computer 102 is able to download EBUHFL 148 from software deploying server 150, including in an on-demand basis. Note further that, in one embodiment of the present invention, software deploying server 150 performs all of the functions associated with the present invention (including execution of EBUHFL 148), thus freeing computer 102 from having to use its own internal computing resources to execute EBUHFL 148.

The hardware elements depicted in computer 102 are not intended to be exhaustive, but rather are representative to highlight essential components required by the present invention. For instance, computer 102 may include alternate memory storage devices such as magnetic cassettes, Digital Versatile Disks (DVDs), Bernoulli cartridges, and the like. These and other variations are intended to be within the spirit and scope of the present invention.

As presented in further detail below, the present invention presents a methodology for identifying ergonomics-based problems facing a user of a computer workstation due to a current real-time body position of the user, and then presenting suggested solutions to the user for correcting these problems. These problems can be recognized by the user himself based on subjective observations, by a computer-recognized layout of the computer workstation, by ambient conditions surrounding the computer workstation, by a computer-identified class of software being used by the user at the workstation, by computer-identified real-time work practices of the user of the computer workstation, and/or by a computer-stored and retrieved personal history of the user of the computer workstation.

Figure 2:
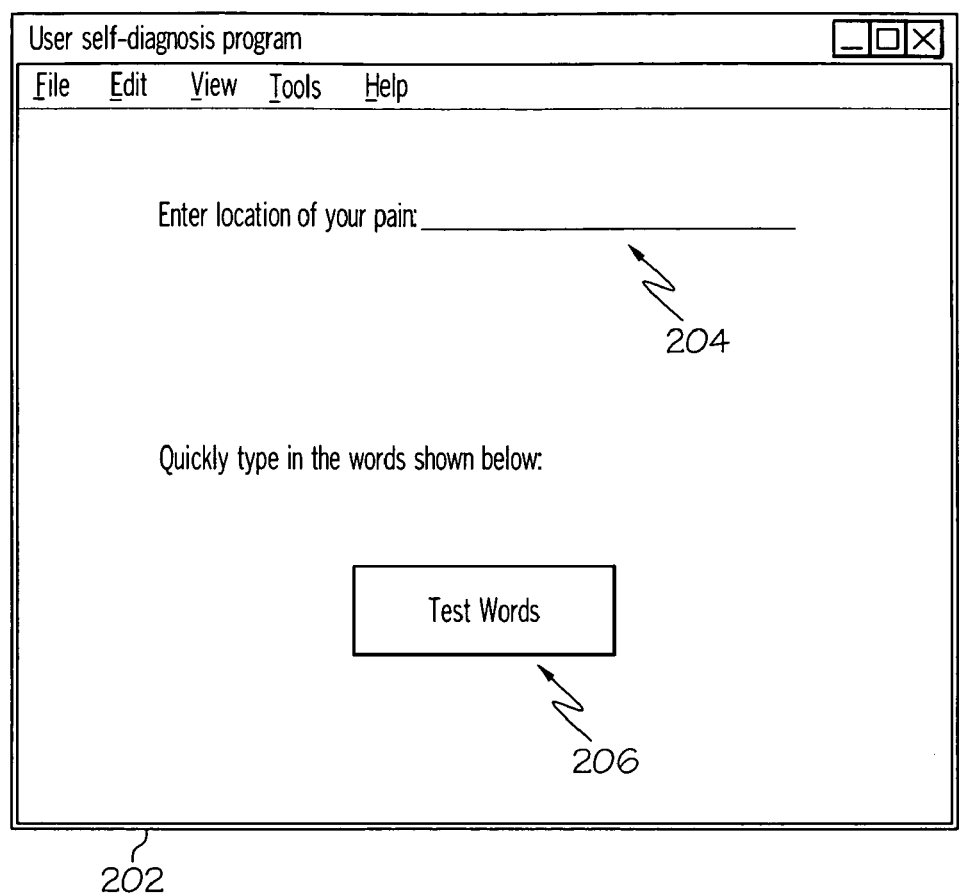
FIG. 2 illustrates a Graphical User Interface (GUI) that permits a user to enter, or to be diagnosed for, ergonomics-related problems.

Referring now to FIG. 2, a Graphical User Interface (GUI) 202 that can be utilized to permit the user to recognize and report ergonomic-based problems is presented. As depicted, GUI 202 presents an entry field 204 in which a user can describe a location of physical body pain. For example, a user may enter "right wrist" in entry field 204. This data entry can be used, in a process described in more detail below, by the EBUHFL 148 introduced in FIG. 1 to determine that there is an ergonomics problem with how the user is utilizing a mouse (not shown in FIG. 2). Similarly, the user may be suffering from a headache or eye strain (which is entered into entry field 204). If so, then a follow-up test can be given on-screen by asking the user to read "Test Words" that are displayed in a shaded window 206, which has a background that makes reading "Test Words" difficult or impossible if eye strain is being suffered by the user.

Figure 3:
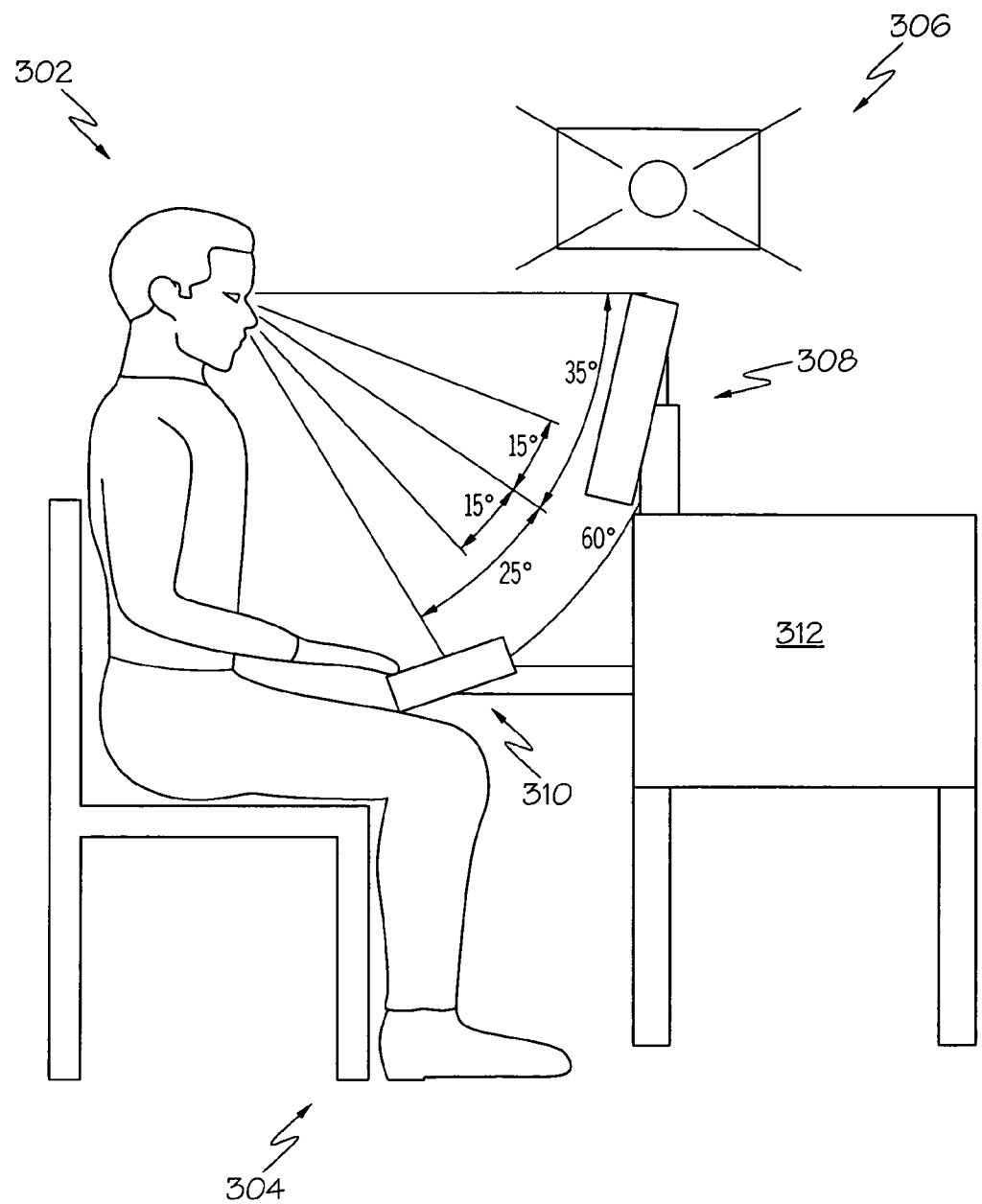
FIG. 3 depicts a user being scanned for improper ergonomic work practices.

With reference now to FIG. 3, an exemplary set-up for identifying ergonomics-based problems by a computer-recognized layout of the computer workstation is presented. As depicted, a user 302 is photographed at a computer workstation 304 by a digital camera 306. The digital camera 306 generates a digital image that can be manipulated to show the user 302's physical orientation and relationship to a monitor 308 and a keyboard 310. That is, a digital image can be manipulated to recognize the user 302, monitor 308, and keyboard 310, and to use trigonometry to calculate their distance and angular orientation among one another and to a desk 312. Similarly, a digital image of the user 302 can be transformed into an avatar, stick figure, or other representation, in order to describe how the posture of the user compares with an ideal and ergonomically correct sitting posture.

Figure 4:
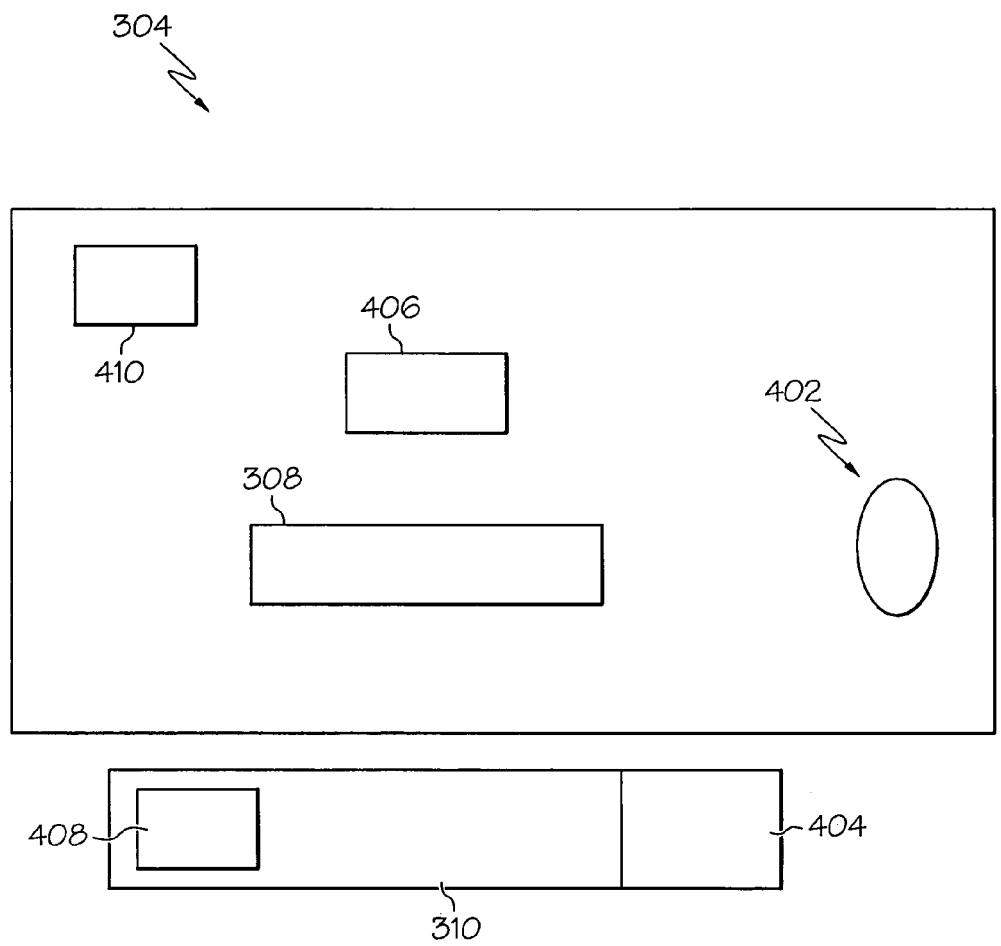
FIG. 4 illustrates a top view of a computer workstation depicted in FIG. 3.

With reference now to FIG. 4, a top-view of the computer workstation 304 introduced in FIG. 3 is presented. Note that a mouse 402 is shown on top of the desk 312, rather than on the more ergonomically correct mouse tray 404. The position of the mouse 402 is detected by a mouse locator 406. Mouse locator 406 may use any reference process available to pinpoint a location of the mouse 402. For example, mouse locator 406 can emit a radio frequency (RF) or infrared (IR) signal that is "bounced back" by the mouse 402. By measuring the Doppler shift and/or timing of the bounced back signal, along with a direction (e.g., through the use of a phased array of antennae) from the mouse locator 402, the mouse detector 406 can determine that the mouse is not on the mouse tray 404, but is rather at an ergonomically adverse location on top of the desk 312.

Other exemplary parameters for identifying ergonomics-based problems facing the user include the following. Ambient conditions of a computer workstation, including the local temperature, can be measured by a digital thermometer 408 and transmitted to a computer 410 (which is wirelessly coupled to the monitor 308, keyboard 310, mouse 402, digital thermometer 408), which utilizes this information in determining what impact the recorded temperature has. For example, if the user is working in a very cold or even an air conditioned environment, this may have an impact on the susceptibility of the user to repetitive stress injuries, such as carpal tunnel syndrome, white finger syndrome, muscle cramps, etc.

Similarly, the computer 410 can recognize what class of software is being used by the user. For example, if a user is merely watching a Digital Video Disk (DVD) movie at his desk, then posture is ergonomically less important than if the user is working with a Computer Aided Design (CAD) program or a word processing program.

In addition, the computer 410 can recognize, identify, and monitor real-time work practices of the user of the computer workstation. As will be describe in more detail, these work practices may include how a keyboard and/or mouse are being used, how long a user is working at a stretch without a break, etc.

Furthermore, the computer 410 can retrieve personal history of the user of the computer workstation, in order to further refine the optimal posture and work practices of the user. Note that such personal history must be carefully utilized. That is, a responsible and confidential use of such information may be properly used to provide "reasonable accommodations" for a person with special needs, or such information may be used in an improper manner to discriminate against such persons. Therefore, care should be taken to ensure the confidentiality and judicious use of such information to ensure that it is only properly used.

The ambient condition, class of software, real-time work practices, and personal history along with all other recorded relevant data relating to the user can be stored in a database in computer 410. The relevant data is used in the formulation of key performance indicators (KPIs), which are used to assess the current ergonomic efficiency of the user. Through use of the recorded and reusable KPIs, EBUHFL 148 can make meaningful recommendations to the user.

Some examples of the use of KPIs to make a meaningful recommendation to the user are as follows:

If the user types an entry describing a tingling sensation in his legs, computer 410 analyzes the current position of the user with a real-time photograph from digital camera 306. A KPI stating that the user is sitting with only his toes touching the floor is registered. EBUHFL 148 then analyzes the KPI using two ergonomic rules: 1) a user's feet should be placed level to the floor and 2) a user's feet should be placed directly in front of the user. EBUHFL 148 then recommends that the user add a foot rest to satisfy the identified ergonomic rules. An explanation may also be sent to the user via GUI 502 (described below) that states that a foot rest will promote even blood circulation in the legs, thus reducing the tingling sensation. The registered KPI is stored as a part of the user's individual and relevant data so that it is available for recollection if the user enters similar data in the future.

Alternatively, a combination of the user's personal history and the current registered KPI may lead EBUHFL 148 to make a different recommendation that will still result in the user following ergonomic rules. If the same KPI is registered (stating that the user is sitting with only his toes touching the floor) but an update to the user's personal history states that the user has a cast on the right leg that must be elevated, EBUHFL 148 uses the personal information to recommend that the user readjust their body alignment and positioning, since the user has taken care to elevate the right leg, but neglected the ergonomic health of the left leg. However, EBUHFL 148 does not recommend that both feet be placed evenly on the floor in front of the body, due to the special circumstances of the user. Similarly, if the user were an amputee, a recommendation in accordance with the ergonomic rules that fit the user's circumstances would be issued, rather than a standard response.

The computer may also recognize a problem based on user work parameters, examples of which are shown and described in FIG. 7 below. The computer registers a KPI stating that the user is sitting too low in a chair, causing the user to sit in an acutely angular position. EBUHFL 148's analysis of the KPI includes the ergonomic rule stating that knees should not be acutely angled (less than 90°) when the user is seated. Combining this with other relevant data, such as the user's height and body alignment, EBUHFL 148 makes a recommendation to adjust the height of the user's chair and/or footrest, if applicable. The user's unique KPI is then stored for future use.

If the user is photographed by digital camera 306 sitting in a C shaped position, EBUHFL 148 recognizes the position as one that does not comply with the ergonomic rule stating that the back should not be slumped when the user is seated or is standing. EBUHFL 148 can then inform the user that he is slumped over, show the correct alignment using GUI 502, and list potential ailments that could result from slumping. The KPI registering the user's slumped position is stored and can be used for future analysis and recommendation.

Figure 5:
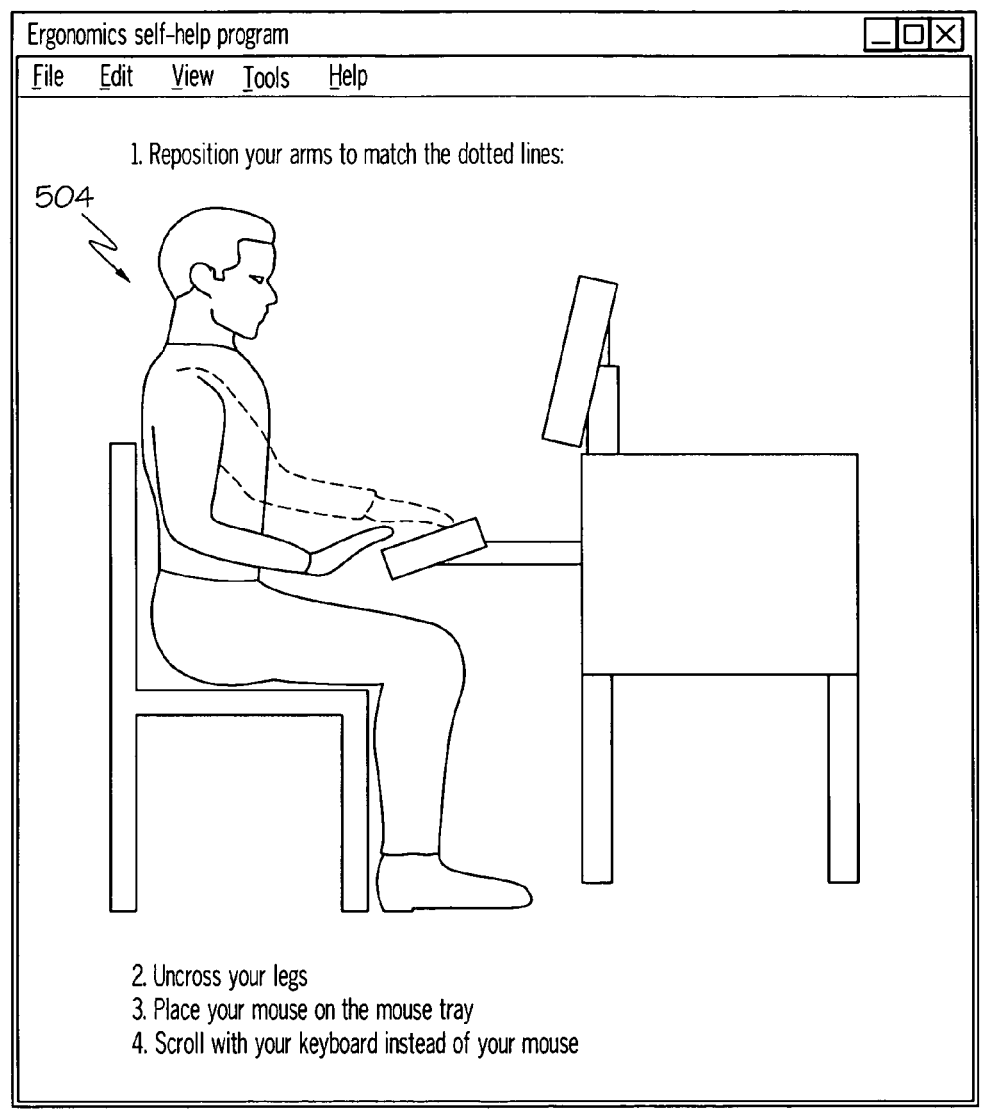
FIG. 5 depicts a GUI presenting recommendations for correcting detected ergonomic problems at a computer workstation.

With reference now to FIG. 5, a second GUI 502 is depicted as showing recommendations that have been tailored to a particular user under real-time conditions for reducing or eliminating ergonomically-related problems. As depicted in the example shown in GUI 502, a stick-figure avatar 504 has been generated showing both the actual posture of the user (generated using inputs from the digital camera 306 shown in FIG. 3) in solid lines, and an optimal posture (shown in dashed lines) for the user, as generated by EBUHFL 148. In the example shown in FIG. 5, EBUHFL 148 has determined that the user needs to adjust his arms, uncross his legs (in order to re-align his spine), use the mouse tray (which the mouse detector 406 shown in FIG. 4 determined was not being done), and to stop using the scrolling wheel (not shown) on the mouse 402, as determined by EBUHFL 148 monitoring the use of functions associated with the mouse 402 depicted in FIG. 4.

Figure 6:
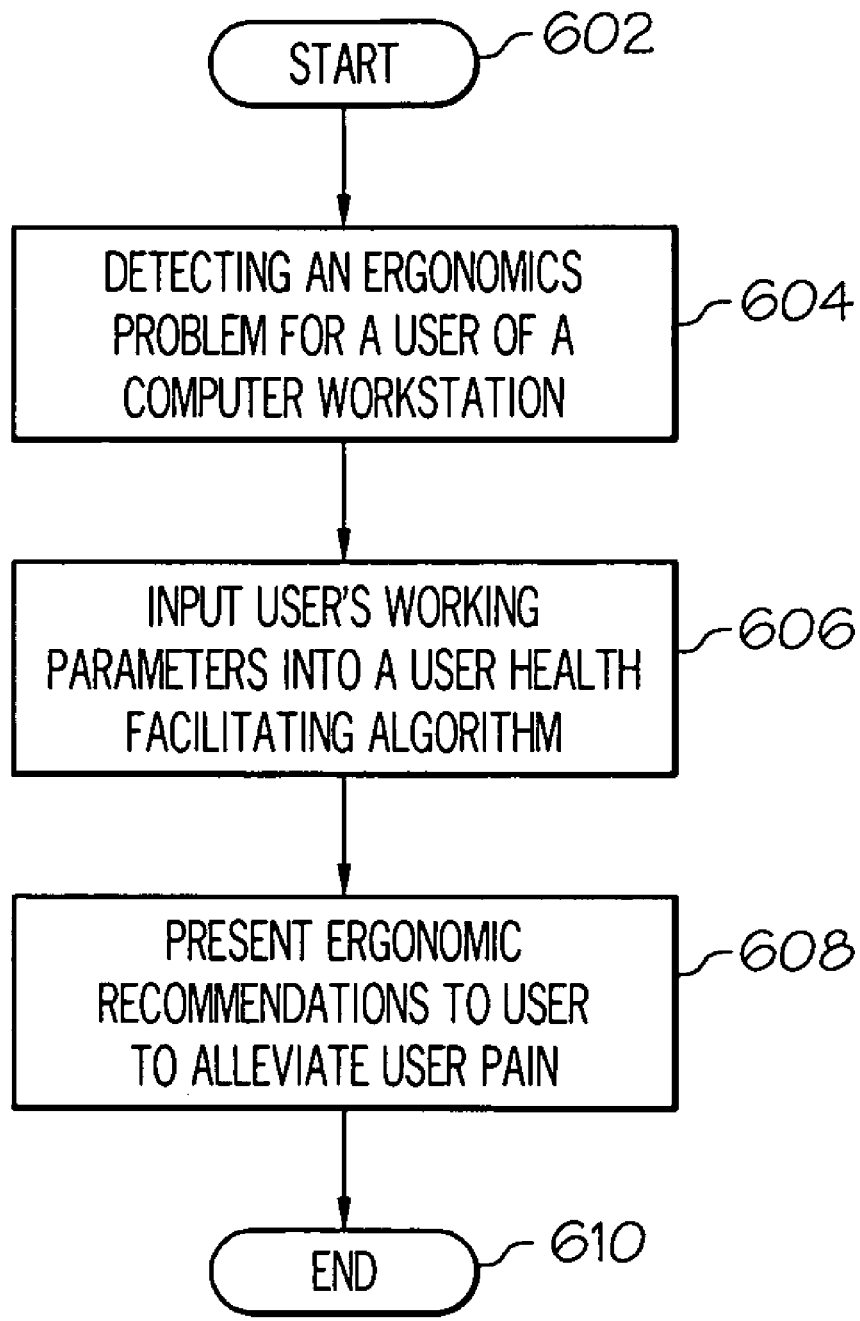
FIG. 6 is a high level flow chart of exemplary steps taken to facilitate ergonomics-based health of a user of a computer workstation.

Referring now to FIG. 6, a high-level flow chart of exemplary steps taken to facilitate ergonomics-based health of a user of a computer workstation is presented. After initiator block 602, which may be prompted by a user opening an ergonomics aid program or window, ergonomics problems are detected for a user of a computer workstation (block 604). These problems may be detected by the user "telling" the computer that he has a problem (e.g., is having pain, as described in FIG. 2), or the computer may recognize the problem for the user according to user work parameters. Examples of how these user work parameters are recognized and stored are shown in FIG. 7.

Figure 7:
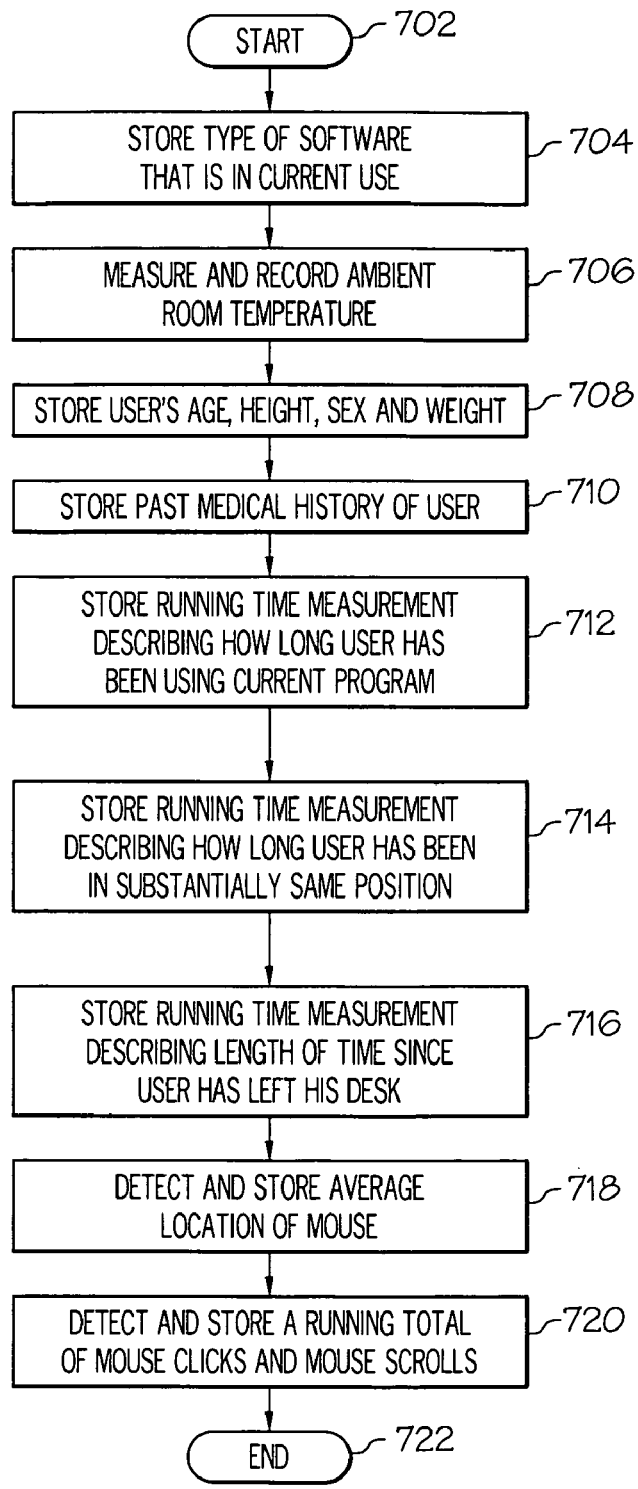
FIG. 7 is a flow-chart of one or more additional steps that can be taken to measure and store user work parameters of a user of a computer workstation.

Referring then to FIG. 7, a flow-chart of one or more additional steps that can be taken to measure and store user work parameters of a user of a computer workstation is presented. After initiator block 702, which can be prompted by the actions describe in block 604 of FIG. 6, the type of software that is being used by the user is detected and stored in the computer (block 704), and particularly in memory associated with EBUHFL 148. Thus, working with software that requires intense concentration and focus on a monitor (e.g., a CAD program) ergonomically requires the user to maintain a different posture than that required for reading webpages.

As depicted in block 706, local air temperature is measured, along with other environmental factors (e.g., light, dust, noise) that may make a user more prone to skeletal-muscular injuries, stress headaches, eye strain, etc., and thus requires a different user posture and/or positioning of the computer workstation.

As described in block 708, personal information about the user (e.g., age, height, sex, weight) are also stored, either from a user input, or from an existing database, for use by EBUHFL 148. This information is utilized to fine-tune the optimal posture exhibited by the user. For example, an older worker may need to be more aware of posture than a younger worker in order to avoid acute muscle cramps. However, both ages of workers should maintain optimal ergonomic posturing in order to avoid chronic problems.

With reference to block 710, relevant medical history of the specific user may also be provided to EBUHFL 148. This information must be kept confidential and used only with the permission of the user. If such conditions are met, then this information can be very useful in tailoring a workstation layout to a particular user, and in assisting that user in maintaining optimal posture. For example, if a user has a history of carpel tunnel syndrome, then that user may be encouraged (via a message displayed on a monitor) to avoid using a scrolling wheel on a mouse, which may exacerbate such a pre-condition.

Referring now to block 712, a running measurement is stored on how long a user has been using a particular program. If a user has been working on a project for two hours, EBUHFL 148 may generate a message suggesting that the user take a short break, in order to allow his body time to "work out any kinks." Similarly, if the user has been in a same position without substantially repositioning for a predetermined period of time (e.g., thirty minutes), then the worker may be reminded to move about (block 714). If the worker has not left his desk for an extended amount of time (block 716), then he may be encouraged to get away from the work station (e.g., if able-bodied, to stand up and walk around) in order to avoid cramping, possible deep vein thrombosis, etc.

In addition, usage of the keyboard, mouse, or other input devices may be monitored as inputs for an ergonomics algorithm executed as EBUHFL 148. For example, the location of the mouse may be detected by a mouse locator (block 718) over some period of time, in order to determine if it is being used in an ergonomically-friendly location. Similarly, if the user is over-using mouse clicks or mouse scrolls (two major causes in skeletal-muscular injuries), this over-usage can be detected (block 720), and these mouse functions may even be temporarily disabled if being overused. The process ends at terminator block 722.

Returning again to FIG. 6, the user's work parameters, including but not limited to some or all of those described in FIG. 7, are input into a user health facilitating algorithm, such as that provided by EBUHFL 148 and described above. Ergonomic recommendations are presented to the user (block 608), either as suggestions (such as shown in FIG. 5), or harmful or potential harmful equipment (e.g., the scrolling wheel on a mouse) may be temporarily disabled, in order to protect the user. The process ends at terminator block 610.

It should be understood that at least some aspects of the present invention may alternatively be implemented in a computer-readable medium that contains a program product. Programs defining functions of the present invention can be delivered to a data storage system or a computer system via a variety of tangible signal-bearing media, which include, without limitation, non-writable storage media (e.g., CD-ROM), writable storage media (e.g., hard disk drive, read/write CD ROM, optical media), as well as non-tangible communication media, such as computer and telephone networks including Ethernet, the Internet, wireless networks, and like network systems. It should be understood, therefore, that such signal-bearing media when carrying or encoding computer readable instructions that direct method functions in the present invention, represent alternative embodiments of the present invention. Further, it is understood that the present invention may be implemented by a system having means in the form of hardware, software, or a combination of software and hardware as described herein or their equivalent.

While the present invention has been particularly shown and described with reference to a preferred embodiment, it will be understood by those skilled in the art that various changes in form and detail may be made therein without departing from the spirit and scope of the invention. For example, while suggestions to the user are shown in FIG. 5 as being depicted in a full-screen GUI 502, a dashboard with "warning lights," icons, or other signals that are understood by the user may be used to display that one or more ergonomic problems have been detected, and/or to display recommended solutions to such ergonomic problems.

Furthermore, as used in the specification and the appended claims, the term "computer" or "system" or "computer system" or "computing device" includes any data processing system including, but not limited to, personal computers, servers, workstations, network computers, main frame computers, routers, switches, Personal Digital Assistants (PDA's), telephones, and any other system capable of processing, transmitting, receiving, capturing and/or storing data.

What is claimed is:

1. A computer-implemented method of facilitating ergonomics-based health in a user of a computer workstation, the method comprising:

a processor detecting an ergonomics problem for a user of a computer workstation, wherein the ergonomics problem is directly related to a current real-time body position of the user, and wherein the ergonomics problem causes an injury to the user if left uncorrected, and wherein the ergonomics problem is detected by detecting a mouse being positioned in an ergonomically adverse location relative to the user, and wherein the ergonomics problem is further detected by an on-screen eye test that detects eye strain currently being suffered by the user;

the processor executing a user health protection algorithm to generate an ergonomic recommendation based on the current real-time body position of the user, the mouse being positioned in the ergonomically adverse location relative to the user, and results of the on-screen eye test, wherein the user health protection algorithm utilizes user work parameters for the user as inputs to the user health protection algorithm, and wherein the ergonomic recommendation corrects the ergonomics problem, and wherein the ergonomic recommendation comprises a recommendation for posture that depends on what type of software is being currently used by the user; and presenting the ergonomic recommendation to the user in the form of two avatars, wherein a first avatar depicts the current real-time body position of the user and a second avatar depicts an optimal ergonomic user posture.

2. The computer-implemented method of claim 1, wherein the detection of the ergonomic problem is prompted by a complaint input from a user, wherein the complaint input describes a location of physical pain being suffered by the user.

3. The computer-implemented method of claim 1, wherein the user work parameters include a type of software being currently used by the user.

4. The computer-implemented method of claim 1, wherein the user work parameters include a real-time measurement of ambient room temperature surrounding the computer workstation.

5. The computer-implemented method of claim 1, wherein the user work parameters include an age, height, sex and weight of the user.

6. The computer-implemented method of claim 1, wherein the user work parameters include a past medical history of user injuries of the user.

7. The computer-implemented method of claim 6, wherein the user injuries are ergonomic-based injuries of the user.

8. The computer-implemented method of claim 6, wherein the user injuries are current injuries of the user.

9. The computer-implemented method of claim 1, wherein the user work parameters include a real-time measurement of how long the user has been using a current program.

10. The computer-implemented method of claim 1, wherein the user work parameters include a real-time measurement of how long the user has remained in a same position at the computer workstation without moving beyond predetermined ranges.

11. The computer-implemented method of claim 1, wherein the user work parameters include a real-time measurement of how long the user has remained at the computer workstation without leaving the computer workstation.

12. The computer-implemented method of claim 1, wherein the type of software being used by the user either requires minimal user interaction or relatively more frequent user interaction, and wherein the user health protection algorithm recommends a more ergonomically correct posture when using software that requires the relatively more frequent user interaction over software that only requires minimal user interaction.

13. The computer-implemented method of claim 12, wherein the software that requires minimal user interaction is a movie, and wherein the software that requires relatively more frequent user interaction is a word processing program.

14. The computer-implemented method of claim 12, wherein the software that requires minimal user interaction is a movie, and wherein the software that requires relatively more frequent user interaction is a Computer Aided Design (CAD) program.

15. A system comprising:
- a digital camera and a mouse locator, wherein the digital camera and the mouse locator detect an ergonomics problem for a user at a computer workstation, wherein the ergonomics problem causes an injury to the user if left uncorrected, wherein the digital camera records an improper posture of the user at the computer workstation, and wherein the mouse locator detects an ergonomically improper location of a mouse relative to the user;
- a monitor for presenting an eye test to the user wherein the eye test determines if eye strain is currently being suffered by the user;
- computing logic for executing a user health protection algorithm to generate an ergonomic recommendation, wherein the user health protection algorithm utilizes user work parameters for the user as inputs, wherein the user work parameters include inputs from the digital camera, the mouse locator, and results of the eye test, wherein the user work parameters also include a stored history of previous ergonomically-related user injuries of the user, wherein the user work parameters also include a current listing of injuries of the user, wherein the ergonomic recommendation comprises a recommendation for posture that depends on what type of software is being currently used by the user, and wherein the ergonomic recommendation corrects the ergonomics problem; and
- a display for presenting the ergonomic recommendation to the user.

16. A non-transitory computer-readable storage medium on which is encoded a computer program, the computer program comprising computer executable instructions configured for:

- detecting an ergonomics problem for a user of a computer workstation, wherein the ergonomics problem is directly related to a current real-time body position of the user, and wherein the ergonomics problem is likely to cause an injury to the user if left uncorrected, and wherein the ergonomics problem is detected by detecting a mouse being positioned in an ergonomically adverse location relative to the user, and wherein the ergonomics problem is further detected by an on-screen eye test that detects eye strain currently being suffered by the user;
- executing a user health protection algorithm to generate an ergonomic recommendation based on the current real-time body position of the user, the mouse being positioned in the ergonomically adverse location relative to the user, and results of the on-screen eye test, wherein the user health protection algorithm utilizes user work parameters for the user as inputs, and wherein the ergonomic recommendation corrects the ergonomics problem, and wherein the ergonomic recommendation comprises a recommendation for posture that depends on what type of software is being currently used by the user; and
- presenting the ergonomic recommendation to the user in the form of two avatars, wherein a first avatar depicts the current real-time body position of the user and a second avatar depicts an optimal ergonomic user posture.

17. The non-transitory computer-readable storage medium of claim 16, wherein the detection of the ergonomic problem is prompted by a complaint input from a user, wherein the complaint input describes a location of physical pain being suffered by the user.

18. The non-transitory computer-readable storage medium of claim 16, wherein the user work parameters include a type of software being currently used by the user.

19. The non-transitory computer-readable storage medium of claim 16, wherein the user work parameters include a real-time measurement of ambient room temperature surrounding the computer workstation.

20. The non-transitory computer-readable storage medium of claim 16, wherein the computer executable instructions are provided by a service provider to a customer in an on-demand basis.

* * * * *